United States Patent [19]
Vivekanandan

[11] Patent Number: 5,777,481
[45] Date of Patent: Jul. 7, 1998

[54] ICE DETECTION USING RADIOMETERS

[75] Inventor: Jothiram Vivekanandan, Boulder, Colo.

[73] Assignee: University Corporation for Atmospheric Research, Boulder, Colo.

[21] Appl. No.: 626,358

[22] Filed: Apr. 1, 1996

[51] Int. Cl.$^6$ .................................................. G01W 1/02
[52] U.S. Cl. .................................... 324/640; 73/170.26
[58] Field of Search ................................. 324/637, 639, 324/640, 643; 73/29.01, 170.26, 170.27; 352/351; 374/122

[56] References Cited

U.S. PATENT DOCUMENTS

| | | | |
|---|---|---|---|
| 4,873,481 | 10/1989 | Nelson et al. | 324/640 |
| 4,978,962 | 12/1990 | Hisasa et al. | 342/351 |
| 5,065,615 | 11/1991 | Hill | 324/640 X |
| 5,231,404 | 7/1993 | Gasiewski | 342/351 |
| 5,381,442 | 1/1995 | Brown et al. | 374/7 |
| 5,526,676 | 6/1996 | Solheim et al. | 73/29.01 |
| 5,654,700 | 8/1997 | Prata | 340/601 |

FOREIGN PATENT DOCUMENTS 0 667 518 A   8/1995   European Pat. Off. ............. 22/4

OTHER PUBLICATIONS

J. Vivekanandan, et al., *Ice Water Path Estimation and Characterization Using Passive Microwave Radiometry*, Journal of Applied Meterology, vol. 30, Oct. 1991, No. 10, pp. 1407–1421.

C. R. Cabrera–Mercader, et al., *Passive Microwave Relative Humidity Retrievals Using Feedforward Neural Networks*, IEEE Transactions on Geoscience and Remote Sensing, vol. 33, No. 6, Nov. 1995, New York, US.

F. Del Frate et al., *Retrieval Of Atmospheric Parameters From Radiometric Measurements Using Neural Networks*, Proceedings 1995 International Geoscience & Remote Sensing Symposium, Firenze, IT, 10–14 Jul. 1995, vol. 2, p. 1134.

C.T. Butler et al., *Retrieving Atmospheric Temperature Parameters For DMSP SSM/T–1 Date With A Neural Network*, Journal of Geophysical Research, vol. 101, No. D3, Mar. 20, 1996.

Pilewskie, P. and Twomey, S., "Discrimination of Ice From Water in Clouds by Optical Remote Sensing," Atmospheric Res., vol. 21 (1987), pp. 113–122. month unavailable.

*Primary Examiner*—Maura K. Regan
*Attorney, Agent, or Firm*—Duft, Graziano & Forest, P.C.

[57] ABSTRACT

A radiometer system detects naturally occurring atmospheric microwave radiation in three bands at approximately 20, 30, and 90 GHz. Signals representing radiation intensity at each of these bands is converted into a brightness temperature and used as a system input to a processing system that yields system outputs including the atmospheric ice water path, liquid water path, and water vapor content. A parameterized radiative transfer model is used to quantify radiation emanating from the atmosphere. The applied signal processing technique provides measurement of the total ice column in the atmosphere, and simultaneously provides accurate measurement of water vapor and liquid water. A calibration technique enhances the accuracy of ice detection measurements by correcting for the effects of absorptive atmospheric components, such as water vapor and liquid water.

25 Claims, 6 Drawing Sheets

ICE DETECTION USING RADIOMETERS

GOVERNMENT FUNDED INVENTION

This invention was made with Government support under Agreement No. ATM-9209181 awarded by the National Science Foundation. The Government has certain rights in this invention.

BACKGROUND OF THE INVENTION

1. Field of the Invention

The present invention pertains to the field of devices or systems that use atmospheric radiation as an indicator of atmospheric conditions. More specifically, the water detection system of the present invention uses a radiometer to measure atmospheric water content including ice content.

2. Statement of the Problem

The earth's atmosphere contains water in the form of water vapor, condensed cloud water, and ice crystals. The ability to measure atmospheric water content is exceedingly useful because it permits mankind to take appropriate action in response to environmental conditions. Atmospheric water content is a key variable that influences aviation, weather prediction, and weather control.

In particular, aircraft pilots want to avoid flying through regions of supercooled liquid water that can form sheets of ice on the exterior wing surfaces of an aircraft. Supercooled liquid water particles or droplets form in the atmosphere as an air parcel rises to a location where the ambient temperature is below 0° C. These droplets have diameters that typically range from tens to hundreds of micrometers, and are known to exist at temperatures as low as −20° C. The droplets adhere to aircraft wing surfaces where they form a sheet of ice. This type of icing continues to be one of the primary causes of aviation accidents, especially in winter weather.

Atmospheric water content data is also needed for use in weather control operations. Clouds are sometimes 'seeded' with fine crystals to induce precipitation. It is desirable to conduct these seeding operations on clouds having a sufficient moisture content to provide the desired precipitation. It is also desirable to optimize the applied concentration of seed crystals for purposes of providing maximum precipitation.

Current techniques for measuring the atmospheric water content from ground based instruments lack reliability under many conditions. The most commonly utilized devices for determining atmospheric water content include radiometers that detect naturally occurring radiation in the atmosphere. The radiometers are designed to sense key frequencies in the water absorption spectrum, and use corresponding mathematical algorithms to estimate the atmospheric water content. Naturally occurring radiation has a fairly even distribution across the earth's surface because down welling radiation from clouds in the presence of a cosmic background behaves similarly to up welling radiation over the cool ocean. These facts permit the use of radiometers over both land and ocean bodies.

Ground-based dual-channel radiometers are commonly used to monitor atmospheric water vapor and cloud water. The resultant radiometric measurements are about the same as or better than measurements that derive from radiosondes which are temporarily deployed into the atmosphere. Ground-based radiometers are preferred over radiosondes because the radiometers advantageously provide continuous automated measurements.

It is presently impossible to provide a system incorporating a physical model that accounts for the many variables which influence ground-based radiometric measurements according to known laws of nature because atmospheric radiation is affected by a series of complex interactions with the atmosphere. Significant variables at least include the relative humidity of the atmosphere at different levels, the bulk density of ice and liquid water, temperature, pressure, radiation scattering due to condensed forms of water, radiation extinction coefficients (or molar absorptivity) of radiation at different frequencies, and the distribution of water and ice particles in the atmosphere. Additionally, some aspects of a purely physical model, e.g., radiation absorption due to a vapor continuum, are not completely understood. Therefore, the most accurate radiometric systems rely upon statistical information that relates ground level microwave radiation readings to atmospheric conditions. In this manner, auxiliary sources of statistical information are used to improve the confidence and accuracy of radiometer measurements. Sources of statistical information include airplanes or probes equipped with sensing instruments, ground-based radar, radio acoustic sounding systems, satellites, and radiosondes.

Radiometric water data retrieval systems typically use statistical models to study data from the atmospheric microwave spectrum. The microwave spectrum is utilized because atmospheric water absorbs other forms of radiation (e.g., near infrared radiation) to emit microwave radiation. These statistical techniques have resulted in the development of various algorithms that indicate water vapor and cloud water information, but these algorithms only relate to conditions where there is no precipitation (e.g., rain or snow). Even so, the statistical systems demonstrate accuracy exceeding that which can be obtained from physical systems.

Most statistical radiometric systems fail to account for the scattering of radiation due to atmospheric water particles, e.g., as water droplets or ice crystals, because the data supporting the system is collected under particle-free conditions. The existing physical and statistical systems break down if precipitation exists as ice or water droplets because the particles introduce a Mie scattering phenomenon (a scattering of light due to particles in the light pathway), while the system models are solely based upon absorption and emission phenomena that fail to account for Mie scattering. For example, water data retrieval accuracies have marginal accuracy if the cloud water content exceeds about 3 mm. In ice clouds, the effect of microwave radiation absorption is negligible, and scattering is the predominant variable influencing the extinction of microwave radiation as the radiation passes through the cloud.

Statistical radiometric systems commonly use brightness temperature measurements from a radiometer as a system input to an algebraic expression that relates statistical brightness temperature input to atmospheric water content output. The term 'brightness temperature' pertains to well known blackbody radiation theory from the field of physics. A blackbody is an ideal body that absorbs all incident radiation and reflects none. Blackbody radiation is the amount of radiant energy that emits from a blackbody at a fixed temperature. Blackbody radiation has a spectral energy distribution that is described by the Planck energy distribution law, which relates blackbody temperature to radiation intensity to bandwidths across a radiation spectrum. A brightness temperature is the temperature of a blackbody that would emit the same amount of radiation energy per unit area in a selected spectral region as is observed from a non-ideal object, e.g., water in the atmosphere. Brightness temperature measurements are within the standard capabilities of substantially all radiometers or radiometer systems in use today. These instruments conventionally detect radiation intensity at a selected band, and use these measurements to derive brightness temperature solutions through the Planck energy distribution law.

The most widely accepted statistical radiometric system uses the model that has been developed by the National Oceanic and Atmospheric Administration ("NOMA"). The NOM model is based upon long term radiosonde information, and varies with the geographical location of the radiometer. Equations (1) and (2) provide a typical dual channel algorithm for the Denver, Colorado area:

$$V = -0.1705 + 0.10368 T_{B20.6} - 0.04526 T_{B31.65} \quad (1)$$

$$LWP = -0.0132 - 0.000879 1 T_{B20.6} + 0.002165 T_{B31.65} \quad (2)$$

wherein V is the integrated water vapor content in cm; LWP is the liquid water path in cm; $T_{B20.6}$ is the radiometer brightness temperature determined at 20.6 giga hertz ("GHz"); and $T_{B31.65}$ is the radiometer brightness temperature determined at 31.65 GHz. It is significant that these algorithms ignore ice water content. The radiosonde data upon which these calculations are based are reasonably accurate for relative humidities ranging between 20% and 90%, but the accuracy is poor for measurements obtained under atmospheric conditions outside this range.

Studies have shown that statistical correlations which produce values of V and LWP from radiometer brightness temperatures have significant variances with respect to the radiosonde data for V and LWP upon which the correlations are based. For example, Wei, Leighton, and Rogers, *A comparison of several radiometric methods of deducing path-integrated cloud liquid water*, 6 J. Atmos. Oceanic Technol. 1001–1012 (1989) reports that a root mean square variance of 8.7% existed between a radiosonde-based correlation similar to Equation (1) (V) for the Nova Scotia, Canada area and the actual radiosonde data upon which the correlation was based. A 37% variance existed for a correlation similar to Equation (2) (LWP).

No method exists to apply radiometric brightness temperatures for the purpose of calculating atmospheric ice content. This analysis is complicated by the fact that microwave emissions from a precipitating cloud undergo a complex interaction with overlapping regions of liquid, melting phase, and ice. Vivekandan, Turk, and Bringi, 30 Journal of Applied Meteorology (No. 10 Oct., 1991) indicates that the difference in brightness temperatures determined at 37 and 85 GHz can possibly be used to estimate the physical properties of an integrated ice water path. A simple system using brightness temperatures obtained from two frequencies was indicated to be potentially useful in predicting the physical properties of an ice water path; however, the theoretical system in many instances showed poor agreement with actual storm data. This article failed to provide a method for using multiple frequencies to calculate atmospheric water parameters, namely, vapor and liquid.

An attempt has been made to overcome the scattering phenomenon by physical modeling. Pilewskie and Towmey, 21 ATMOSPHERIC RESEARCH 113–122 (1987) applies a simple geometric optics approximation for single-scattering albedo to show that polydispersed distributions of water and ice have dramatically different absorptions within portions of the near infrared spectrum. A comparison between near infrared measurements from two clouds shows that the clouds had different near infrared absorptions. It was suggested that the absorption differences were caused by the presence of ice in one of the clouds; however, the technique could not provide quantitative measurements of cloud ice and water contents.

There remains a need for a radiometer system that can simultaneously with reliability determine the amount of atmospheric water vapor, cloud water, and ice. Atmospheric ice content is especially difficult to determine using conventional methods and apparatus.

SOLUTION

The system of the present invention overcomes the problems mentioned above, and provides a significant advance in the art by providing a radiometric water detection system that can reliably determine the amount of atmospheric water vapor, cloud water, and ice. The system method and apparatus detects radiation at multiple frequencies, and uses the radiation data to as system input to a processor system that calculates the relative amounts of atmospheric water vapor, cloud water, and ice. The system provides superior accuracy because it accounts for the scattering effects of ice particles.

In its broadest sense, the radiometric water detection system of the present invention is one that is able to quantify the presence of atmospheric ice. The detection system includes a radiometer that passively detects naturally occurring atmospheric microwave radiation in a plurality of bands. The radiometer provides signals that represent the detected radiation for each of the bands. These signals are converted to brightness temperatures, which are used as system inputs to a computerized neural network that yields system outputs indicative of the observed data including atmospheric ice water path, liquid water path, and water vapor content.

Use of the neural network, while not absolutely essential to the invention, is much preferred because of the wide-ranging flexibility and ease of operation that are associated with its use. Neural networks provide a relationship between any input -data set and any output data set in ways that purely statistical correlations cannot. For example, neural networks can provide these relationships for non-linear functions. Statistical models can also fit non-linear data clouds, but a statistician typically has to introduce personal bias into the model to gain this effect. Additionally, nonlinearities are not always apparent from a review of the data.

In preferred embodiments, the radiometric water detection system detects microwave radiation in a plurality of bands that are particularly sensitive to specific phases of atmospheric water. For example, a 20.6 GHz band is mostly sensitive to water vapor, a 31.65 GHz band is mostly sensitive to liquid water, and a 90 GHz band is sensitive to the particle scattering effects of ice. Thus, the frequencies of interest are selected to conform with the radiative absorption and emission spectrum of water.

The radiometric water detection system is preferably trained from a synthetic data set by using a data set derived from a forward-looking radiative transfer model. The radiative transfer model combines physical laws with statistical data to produce the synthetic data set. Thus, the forward-looking radiative transfer model incorporates such items as theoretical microwave extinction due to the Mie scattering effects of atmospheric ice particles, statistical correlations relating radiosonde data to observed brightness temperatures, and radiation extinction due to water vapor absorption.

In especially preferred embodiments, the number of variables represented in the synthetic training data set are limited to those having the greatest effect or sensitivity to the presence of atmospheric water. A comparative sensitivity study is used identify and cull non-sensitive variables. The complexity of the system analysis of the radiometric water detection system is, accordingly, reduced by selecting for analysis only those variables that are most sensitive to atmospheric water.

The system training using the synthetic data set preferably occurs by introducing the forward-looking radiative transfer model synthetic data set together with associated brightness temperatures into a neural network. In the training process, the neural network adjusts its weighting factors to accept brightness temperature measurements at a plurality of frequencies or wavelengths, and provide output including atmospheric water content including ice water path, liquid water path, and water vapor column.

The radiometric water detection system preferably calibrates itself by calculating a mean difference in brightness temperatures between the neural network system output and physical observations by secondary means (.e.g., data from statistical correlations that work very well in selected atmospheric conditions). The calibration or correction is performed by adjusting the incoming data to reflect an average difference between the neural network system output and the data from the secondary means. The adjusted synthetic data set is use to retrain the neural network for enhanced accuracy.

Other salient features, objects, and advantages will be apparent to those skilled in the art upon a reading of the discussion below in combination with the accompanying drawings.

DETAILED DESCRIPTION OF THE PREFERRED EMBODIMENT

Figure 1:
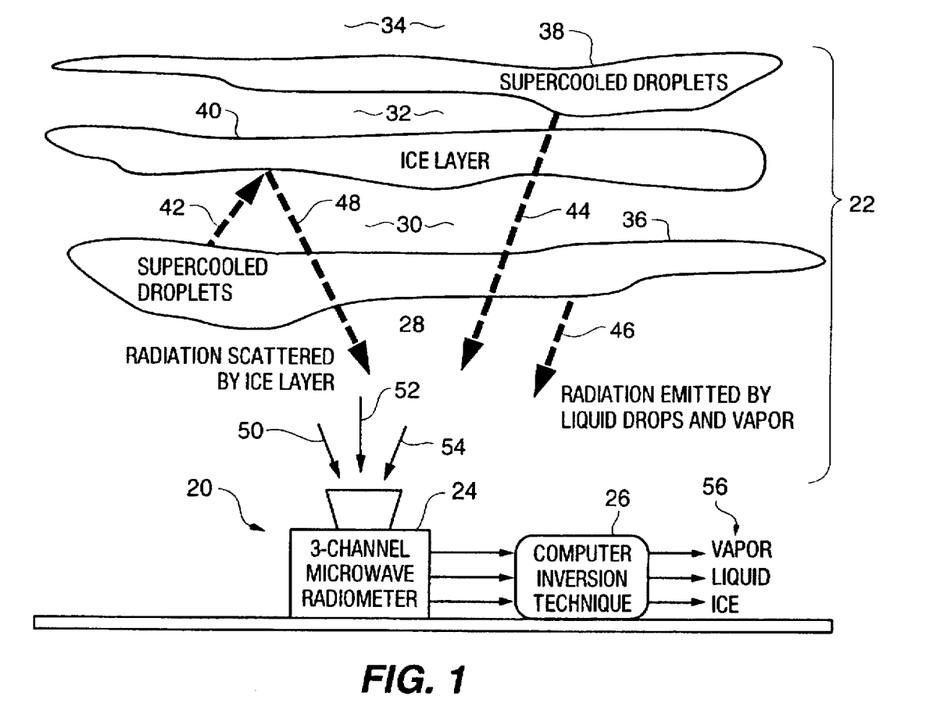
FIG. 1 depicts a radiometer system including a computerized neural network system according to the present invention.

FIG. 1 depicts a conceptual diagram of a radiometric water detection system 20 according to the present invention in its intended environment of use as a ground based system used to measure the water content of atmosphere 22. The major components of radiometric water detection system 20 include a three channel ground-based microwave radiometer 24 and a computer 26.

The majority of the discussion below pertains to a signal processing method that provides simultaneous estimation of atmospheric vapor, liquid, and ice content. Computer 26 incorporates a program that receives signals from radiometer 24 and processes these signals to achieve the desired results. A neural network in computer 26, accordingly, converts system inputs into system outputs that at least include the atmospheric water vapor content, the atmospheric liquid water content, and the atmospheric ice content. The operational principles of radiometer 24 and computer 26 are discussed before describing the neural network system because an understanding of these operational principles facilitates an understanding of the mathematical system.

RADIOMETER OPERATION

Radiometer 24 functions according to the conventional principles of radiometer operation. Conventional radiometers utilize at least two channels to detect microwave radiation at 20.6 GHz and 31.65 GHz according to NOAA guidelines, or they can operate on one channel. One example of a commercially available dual-channel radiometer is the WVR—1100 model, which is can be purchased from Radiometrics, Inc. of Boulder, Col. Other radiometers that detect additional frequencies of microwave radiation (e.g., three channel radiometers) can be supplied on commercial order from a variety of manufacturers, such as Radiometrics, Inc. Generally, companies that provide radiometer equipment offer commercially available services that permit the addition of extra channels (i.e., detection frequencies as specified by the customer) into conventional radiometer equipment. These companies also manufacture radiometer equipment that detects radiation at selected user-specified frequencies.

Radiometer 24 is used to detect naturally occurring microwave radiation from atmosphere 22. Atmosphere 22 includes a plurality of water vapor regions 28, 30, 32, and 34 in which there exists water vapor and substantially no liquid water or ice. Atmosphere 22 also includes liquid water clouds 36 and 38, which are formed of supercooled liquid water droplets. Ice cloud 40 is formed of tiny ice crystals that are suspended in the atmosphere. Water clouds 36 and 38 absorb naturally occurring near infrared radiation and emit corresponding microwave radiation along a plurality of pathways, such as exemplary pathways 42, 44, 46. In the case of pathway 42, contact with ice cloud 40 causes a reflective scattering of microwave radiation along pathway 48 due to Mie scattering as the radiation along path 42 impinges upon the ice crystals in cloud 40. The radiation intensity decreases along pathway 44 as the radiation sequentially passes through water vapor region 32 where water vapor absorbs a portion of the microwave radiation, ice cloud 40 where a portion of the radiation is scattered, water vapor region 30 where microwave radiation is again absorbed, water cloud 36 where a portion of the radiation is absorbed by water droplets and water vapor, and water vapor region 28. The atmospheric configuration shown in FIG. 1 is exemplative, and other atmospheric conditions can exist in different naturally occurring layer patterns, such as no clouds, ice clouds only, water clouds only, or additional water and ice clouds. Thus, the naturally occurring microwave radiation in atmosphere 22 potentially undergoes many complex interactions before it impinges upon radiometer 24.

A representative portion of the microwave radiation from atmosphere 22 impinges upon radiometer 24 as system inputs 50, 52, and 54. Each channel of the three channel radiometer 24 is dedicated to a specific frequency band corresponding to one of system inputs 50, 52, and 54. Radiometer 24 detects the impinging microwave radiation for each band in a conventional manner. The total microwave radiation is filtered to select channels corresponding to the desired frequencies for study. It is preferred that radiometer 24 is oriented in a precise vertical orientation to receive radiation only from the portion of the atmosphere that exists in direct vertical alignment with radiometer 24 (i.e., radiometer points substantially upward, neither to the right nor to the left).

System inputs 50, 54, and 56 include three radiation bands that constitute portions of the total microwave radiation impinging upon radiometer 24. The three channels of radiometer 24 independently detect the intensity of the bands corresponding to system inputs 50, 54, and 56. These bands are preferably selected to include microwave radiation frequencies in a first band ranging from 20 to 21 GHz, a second band ranging from 30 to 32 GHz, and a third band ranging from 89 to 91 GHz. These bands are respectively referred to herein as the 20 GHz, 30 GHz and 90 GHz bands. The most preferred frequencies for each band are 20.6 GHz for the 20 GHz band, 31.65 GHz for the 30 GHz band, and 90 GHz for the 90 GHz band.

The three different frequencies of the 20 GHz, 30 GHz, and 90 GHz bands are selected for their corresponding sensitivities to environmental conditions. The 20.6 GHz frequency is offset from a weak water vapor resonant line at 22.235 GHz in the water vapor absorption spectrum. Detection of this frequency at radiometer 24 provides a measurement that primarily relates to integrated atmospheric water vapor, and is not very sensitive to environmental conditions including pressure and areas of different water vapor concentration. Similarly, the 31.65 GHz frequency is primarily sensitive to liquid water in the atmosphere. The 90 GHz frequency is sensitive to Mie scattering as the radiation impinges upon water droplets or ice crystals.

Radiometer 24 detects radiation corresponding to the intensity of system inputs 50, 52, and 54 in the form of voltage signals, and converts these signals to digital signals that are transferred to computer 26. Computer 26 receives the digital signals from radiometer 24 and processes the signals to obtain brightness temperatures for each channel in a conventional manner. Alteratively, radiometer 24 processes its own digital signals to obtain brightness temperatures, and transfers signals representing the brightness temperature to computer 26. As indicated above, computer 26 applies the brightness temperatures to a mathematical or neural network system that processes the brightness temperatures to provide system outputs 56 (see FIG. 1) including the atmospheric content of water vapor, liquid water, and ice, as well as other descriptive information concerning these three water states. Computer 26 preferably stores the system input and output values for later use as needed.

THE NEURAL NETWORK SYSTEM

Figure 2:
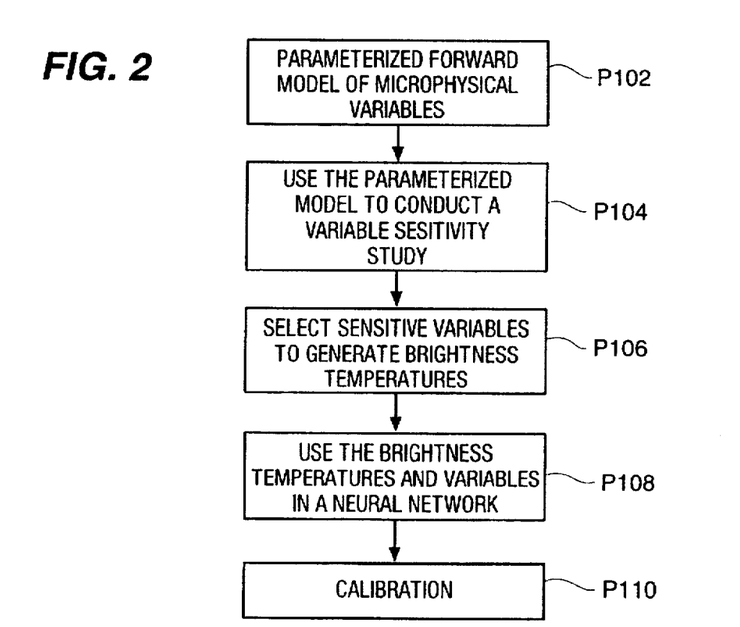
FIG. 2 depicts a process flow chart diagram that governs the development of the neural network system for the FIG. 1 system.

FIG. 2 depicts a schematic process diagram that provides a generalized overview of a process 100 that is used by the system 20 of the present invention.

Computer 26 is preferably programmed to implement all of the steps in FIG. 2. In FIG. 2 generally, steps P102, P104, and P106 are used to generate a synthetic data set that derives from a combination of physical laws and statistical data. This data set is used in step P108 to train a neural network algorithm that can apply radiometric measurements as system inputs to yield values describing atmospheric conditions including water content. Computer 26 of FIG. 1 incorporates this model, and uses it to process signals received from radiometer 24 to determine atmospheric water content. Additional details pertaining to some of the steps are provided below in the context of additional figures and examples.

Step P102 pertains to the implementation of a forward radiative transfer system that uses mathematical equations to describe atmospheric conditions. The equations include physical laws of nature, relationships that approximate physical laws of nature, and statistical data. The equations relate inputs and outputs as a plurality of microphysical variables that influence the calculation of brightness temperatures; however, it is characteristic of the extinction of radiation passing through the atmosphere that no one equation affords a comprehensive solution.

Thus, step P102 includes the identification and selection of any equation that relates to or could relate to the effects of water in the atmosphere.

In Step P104, the microphysical variables are varied one at a time, and corresponding brightness temperatures are calculated to determine the sensitivity of the brightness temperature calculation to the microphysical variable under study.

In step P106, the microphysical variables that most significantly affect brightness temperatures are selected for further study. The non-selected variables are held constant at a reasonable value while the selected variables are altered within reasonable ranges to generate a data set including brightness temperatures corresponding to the sensitized variable set. This step simplifies the system by considering only the most significant variable to reduce unnecessary complexity.

In Step P108, the brightness temperature data set from step P106 is applied to a neural network algorithm to generate a neural network modeling system. The model accepts system inputs including radiometer-based brightness temperature measurements, and provides system outputs representing atmospheric water content.

In step P110, the neural network solution is calibrated to make the neural network solutions agree more closely with field conditions. The resultant system is loaded into computer 26 (see FIG. 1) for operations in cooperation with radiometer 24.

THE PARAMETERIZED MODEL

Figure 3:
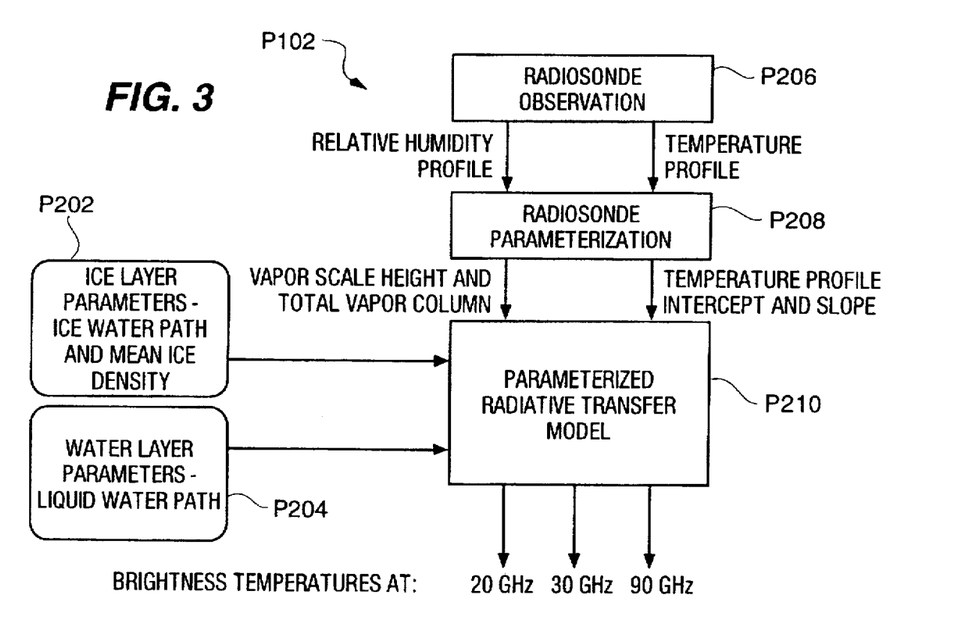
FIG. 3 depicts a process flow chart that illustrates a portion of the FIG. 2 process in greater detail.

FIG. 3 depicts a schematic process diagram providing additional detail with respect to Step P102 of FIG. 2. The significance of this model is that it relates microphysical parameters in the atmosphere to the transmission of radiation through the atmosphere under a variety of conditions. Thus, a very large number of data points are advantageously created through use of the model without having to fly test instrumentation through the atmosphere. The parameterized model is a precursor of the neural network system that is loaded into computer 26.

The FIG. 3 process yields a parameterized forward-looking radiative transfer system that is used to generate a set of brightness temperature data from statistical data in combination with physical modeling. In developing the radiative transfer system, assumptions are sometimes made for purposes of simplification, and these assumptions are identified below. Errors that are introduced to the system by these assumptions are removed in the calibration step P110.

In step P202, equations are selected that relate microphysical parameters to ice water path and mean ice density. Generally, these equations attempt to explain or simulate special aspects of atmospheric behavior. Those skilled in the art can select a variety of equations for testing and implementation in the forward-looking radiative transfer model, and understand that the preferred equations described below may be supplemented or substituted. Equations (3)–(6) below are especially preferred for use in step P202.

A modified gamma function according to Equation (3) is preferably used to describe the size distribution of ice crystals or liquid water particles, which are assumed to be spherical:

$$n(r) = ar^\alpha \exp(-br^\gamma) \quad (1)$$

wherein n(r) is the number of particles per unit volume per unit radius; r is the radius of the particles; and parameters a and y are set to two ($\alpha$) and one ($\gamma$). The parameters a and b are defined by Equations (4) and (5) as:

$$a = \frac{b^6}{160\pi \rho_i} IWC \quad (4)$$

$$b = \frac{2}{r_c} \quad (5)$$

wherein $r_c$ is mode radius of the particles; $\rho_i$ is the mean bulk ice density; and IWC is ice water content. The ice water path IWP is calculated as the integral of IWC at a given height z determined with respect to height across the ice region, or $$IWP = \int_{Z_{bot}}^{Z_T} IWC(z)dz \quad (6)$$

wherein $z_t$ and $z_{bot}$ represent the top and bottom of the ice region; and z represents a height above the surface of the earth.

In step P204, the modified gamma distribution of Equation (3) is used to predict the liquid water content LWC of droplets in a liquid water region. In this case where a water cloud exists, Equation (7) relates LWC to parameter a:

$$a = \frac{b^6(LWC)}{160\pi \rho_w} \quad (7)$$

wherein $\rho_w$ is the mean bulk water density; and LWC is liquid water content. The liquid water path LWP is obtained by substituting LWC for IWC in Equation (6) for the water region.

In step P206, radiosonde observations are preferably used to identify a relative humidity profile and a temperature profile for the atmosphere. Radiosondes are used to measure vertical profiles of relative humidity (or vapor density), absolute pressure, temperature, and dew point in the lower atmosphere.

Figure 4:
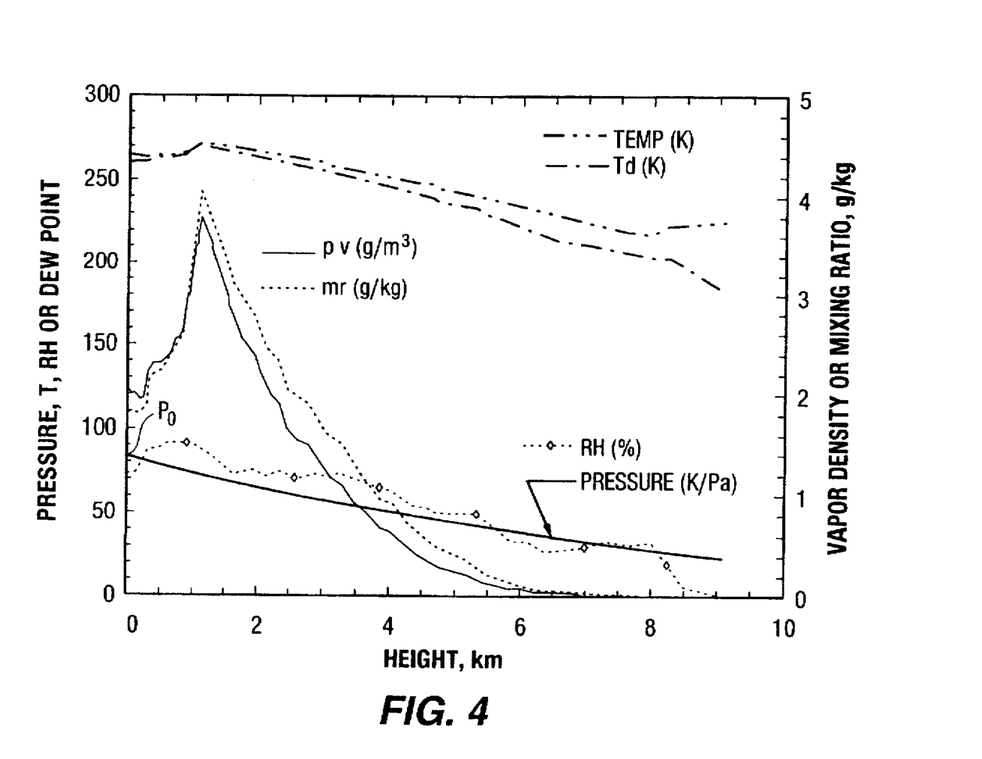
FIG. 4 depicts a plot of data derived from radiosonde measurements, and which is used in developing the system according to the FIG. 2 process.

FIG. 4 depicts exemplary results of radiosonde measurements for use in step P206. A temperature profile is calculated from this data according to Equation (8):

$$T(z) = T_c - \Gamma z \quad (8)$$

wherein T(z) is the atmospheric temperature at a height z above the surface of the earth; $T_A$ is the near surface atmospheric temperature determined from the radiosonde temperature data of FIG. 4 according to Equation (9); and $\Gamma$ is the temperature gradient or lapse rate computed from the radiosonde data of FIG. 4 according to Equation (10). According to Equations (9) and (10):

$$T_A = 4\bar{T} - 6T_\sigma \quad (9)$$

$$\Gamma = 6/H|\bar{T} - 2T_\sigma| \quad (10)$$

wherein H is the thickness of the lower atmosphere; $\bar{T}$ is the mean of the temperature profile calculated according to Equation (11) below; and $T_\sigma$ is the first moment of the temperature profile calculated according to Equation (12) below. According to Equations (11) and (12):

$$\bar{T} = \frac{1}{H} \int_0^H T(z)dz \quad (11)$$

$$T_\sigma = \frac{1}{H^2} \int_0^H zT(z)dz \quad (12)$$

In step P208 (see FIG. 3), the radiosonde data is further parameterized by calculating an integrated or total vapor column and a vapor scale height. Equation (13) below provides the calculation for bulk vapor density PVI and equation (14) provides the integrated vapor column V:

$$\rho_v = \frac{V}{H_v} \exp\left(-\frac{z}{H}\right) \quad (13)$$

$$V = \int_0^H \rho_v(z) \quad (14)$$

wherein $\rho_v$ is the water vapor density, and the other variables are defined above. Equation (15) provides the calculation for the vapor scale height $H_v$:

$$H_v = \frac{\int_0^H z\rho_v dz}{\int_0^H \rho_v dz} \quad (15)$$

In step P210, the microphysical parameters derived from Equations (3) through (15) are used to calculate the extinction of microwave radiation as it travels through the atmosphere. The values from the model are applied to a generalized radiative transfer model to estimate the relationship between atmospheric conditions and the intensity of radiation impinging upon radiometer 24 (see FIG. 1) Information pertaining to the transfer of radiation through the atmosphere and the conventional use of finite difference techniques to calculate this transfer according to a generalized radiative transfer equation is found in various literature, e.g., Tsang, Kong and Sain, *Theory of Microwave Remote Sensing*, John Wiley & Sons, New York (1985). The extinction of microwave radiation occurs due to water vapor absorption, air absorption, liquid water absorption, and ice scattering. The system computes these values over an optical pathway through atmosphere 22 to radiometer 24 (see FIG. 1). The calculation results include the amount of radiation impinging upon radiometer 24 from the respective 20, 30, and 90 GHz bands. The impinging radiation values are converted into brightness temperatures for each of the three bands. The following paragraphs provide a brief discussion of the step P210 application of this technique in the context of Equations (16)–(20).

The gaseous absorption within atmosphere 22 (see FIG. 1) is calculated according to the conventional Liebe's unified millimeter wave propagation system as described by Liebe, MPM-An atmospheric millimeter-wave propagation model, 10 INT. J. Infrared Millimeter Waves 631–650 (1989). This system computes the microwave extinction coefficient c of dry air and water vapor as a function of temperature, pressure, and humidity. The radiosonde data includes water vapor density $\rho_v$ as a function of height. For vapor regions 28, 30, 32, and 34, the radiosonde $\rho_v$ data is preferably converted into relative humidity RH according to Equation (16):

$$RH = \frac{e}{2.4089} \left(\frac{T}{300}\right)^5 \times 10^{\frac{2950.2}{T} - 10} \quad (16)$$

wherein T is the physical temperature. The parameter e is the partial water vapor pressure given by the gas law:

$$e = \rho_{sa}(z)RT \quad (17)$$

wherein $\rho_v(Z)$ is water vapor density as a function of height z; T is temperature, and R is the molar gas constant. In ice and water regions, the relative humidity is assumed to be 100%.

The transfer of electromagnetic radiation through the atmosphere is described by the radiative transfer equation. There are four processes that can change the intensity as it passes through the atmosphere: (a) radiation can be absorbed; (b) radiation can be limited; Ĉ radiation can be scattered into other directions, and (d) radiation from other directions can be scattered into the beam. Combining the above-mentioned terms, the radiative equation is:

$$\frac{dI}{dS} = \sigma_a I - \sigma_s I + \sigma_a B(T) + \quad (18)$$

$$\frac{\sigma_s}{4\pi} \int_0^{2\pi} \int_0^{\pi} I(\theta^1, \phi^1) \rho(\theta^1, \phi^1; \theta, \phi) \sin\theta^1 d\theta^1 d\phi^1$$

Where s is distance along the path, I is intensity, $\sigma_a$ is the volume absorption coefficient; $\theta$ is the value scaling coefficient, $\rho)\theta$, $\phi$; $\theta^1$, $\phi^1$) is the scattering phase function; angles ($\theta^1$, $\phi^1$) are the direction of incoming radiation; and ($\theta$, $\phi$) are the outgoing direction of radiation from the atmosphere. The above equation can be rearranged as:

$$\frac{dI}{dS} = \sigma_a [B(T) - T(\theta,\phi)] + \sigma_s [<> - I] \quad (19)$$

In the absence of ice particles, $\sigma_s$ is zero, and the radiative transfer equation simplifies as:

$$\frac{dI}{dS} = \sigma_a [B(T) - I(\theta,\phi)] \quad (20)$$

The modified Gamma distribution of Equation (3) is used to average scattering of ice particle ensembles. The refractive indices of liquid water droplets and ice particles at the needed frequencies are obtained by interpolating tabulated values from published sources, e.g., the values reported in Ray, Broadband complex refractive indices of ice and water, 11 Applied Optics 1836 (1972). Thus, Equation (19) is used to calculate the portion of microwave radiation I that is transmitted from a source having an intensity $I_o$ to radiometer 24 through a field of scattering particles having a distribution according to Equation (3).

The conventional invariant embedding method reported by Tsang, Kong, and Shin, Theory of microwave remote sensing, New York, John Wiley & Sons (1985) is preferably applied to find the solution to the radiative transfer equation. According to this method, an arbitrarily defined vertical structure is divided into a number of homogenous layers. The radiative transfer equation for each layer is rewritten in the form of finite difference calculations and Gaussian quadrature integral formulae taking advantage of the principle that adjacent layers interact with one another to transmit radiation. The formulation of radiative transfer includes reflection matrices, transmission matrices, and emission source vectors of the entire atmosphere, and also includes selected boundary conditions. These boundary conditions permit the computation of outgoing radiation and the radiation field inside the medium. The invariant embedding method, accordingly, provides a value for the intensity of radiation from the 20, 30, and 90 GHz bands impinging upon radiometer 24.

The impinging radiation values are converted into corresponding brightness temperatures by conventional radiometric processing techniques. The techniques apply black body radiation theory to assume that the radiation impinging upon radiometer 24 originates from a black body, and compute the temperature of the black body which would emit an equivalent amount of radiation. The calculations preferably apply the well known Planck distribution law.

As indicated above, step P104 of FIG. 2 includes a sensitivity study of the parameterized model to changes in brightness temperature values that are applied to different parameters.

Examples 1 below describes preferred calculations for use in the sensitivity study after the parameterized model has been selected. Specifically, Example 1 provides an example of Steps P102 through P106 in FIG. 2.

EXAMPLE 1

SENSITIVITY STUDY

Figure 5:
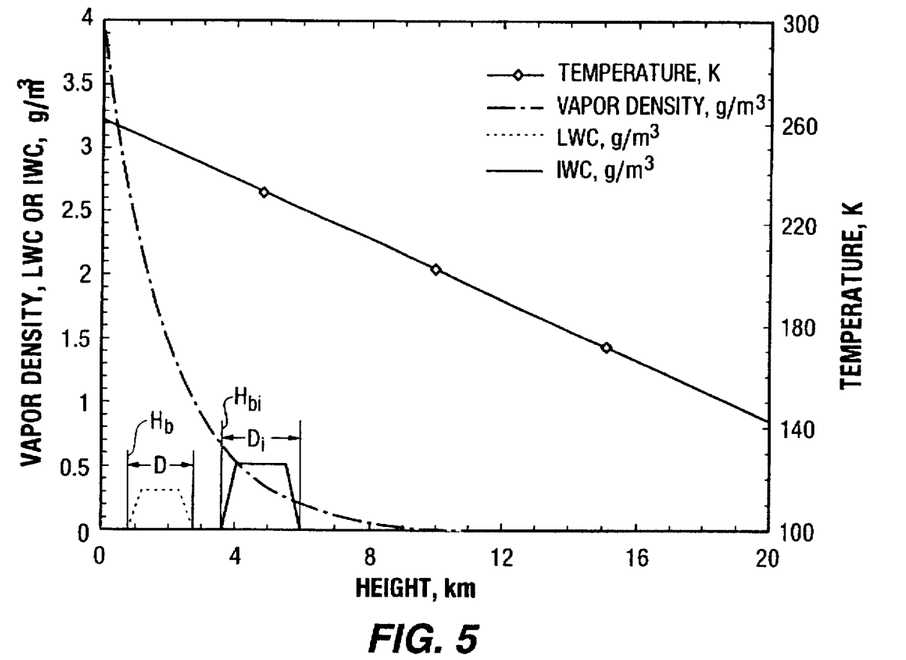
FIG. 5 depicts a parameterized structure that is used to develop the system according to the FIG. 2 process.

Referring to FIG. 2, Equations (3)–(20) were programmed to obtain computer software incorporating a radiative transfer model. FIG. 5 depicts an atmospheric water profile that was followed to guide the sensitivity study according to the invariant embedding method of Tsang, Kong, and Shin, They of microwave remote sensing. FIG. 5 shows parameterized atmospheric structure or conditions derived from Equation (9). Alteratively, equivalent data may be provided as radiosonde data, if such data is available. The water vapor density measurements preferably derive from radiosonde data. A water cloud is located at a height between one and three km, and has a cloud thickness D beginning at water cloud base $H_b$. Similarly, an ice cloud is located at a height between about four to six km, and includes an ice cloud thickness D, beginning at ice cloud base $H_{bi}$.

The boundary conditions for the invariant embedding method were selected as land surface having an emissivity of 0.95, a ground temperature equal to the effective near surface temperature $T_A$, and a top boundary temperature equaling 2.7° K. due to incident radiation. These values were arbitrarily selected by an expert to represent reasonable values for actual field conditions. The sensitivity study was conducted over three channels, i.e., at 20.6, 31.65, and 90 GHz. A base state was selected to represent average wintertime conditions in Denver, Col., and the sensitivity study was conducted around this base state. Table 1 below provides the base state and example sensitivity results. Sensitivity to a given variable is given as the partial derivative of the brightness temperature at each frequency taken with respect to the parameter. The Table 1 values for these derivatives represent average values over the interval studied. The Table 1 results represent the completion of step P104 in FIG. 2, i.e., a completed sensitivity study.

TABLE 1

| Parameter | Base State | $\frac{\delta T_{B20.6}}{\delta p}$ | $\frac{\delta T_{B31.65}}{\delta p}$ | $\frac{\delta T_{B90}}{\delta p}$ | Units | Sensitivity Class |
|---|---|---|---|---|---|---|
| V | 0.8 cm | 7.0 | 4.3 | 16.3 | K/cm | High |
| LWP | 0.2 mm | 31.0 | 62.5 | 199.0 | K/mm | High |
| IWP | 0.2 mm | 5.0 | 14.0 | 64.5 | K/mm | High |
| $P_o$ | 84.0 KPa | 0.06 | 0.13 | 0.27 | K/KPa | Medium |
| $\rho$ | 0.92 g/cm$^2$ | 1.49 | 4.5 | 17.5 | K cm$^3$/g | Medium |
| $r_e$ | 0.05 cm | 20.0 | 33.0 | 51.0 | K/cm | Medium |
| D | 1.0 km | 0.6 | 1.0 | 0.2 | K/km | Low |
| $D_i$ | 1.0 km | −0.05 | −0.05 | −0.15 | K/km | Low |
| $H_{bi}$ | 4.0 km | −0.05 | −0.05 | −0.03 | K/km | Low |
| $\Gamma$ | 6.5° C./km | 0.25 | 0.7 | −0.2 | K km/C | Low |
| $T_A$ | 0° C. | −0.02 | −0.3 | 0.2 | K/C | Low |
| $H_b$ | 1.5 km | 1.0 | 1.7 | 0.3 | K/km | Low |
| $H_t$ | 2.0 km | −0.8 | −0.6 | −2.1 | K/km | Low |

Step P106 was completed by reviewing the Table 1 results to conclude that the radiative transfer system was highly sensitive to V, IWP, and LWP. Other variables were indicated to have a moderate or low sensitivity. In Table 1, the Sensitivity Class column provided an arbitrary distinction between the different variables. Generally, it was preferred to simplify the overall modeling process by focusing only upon the variables that are most likely to influence brightness temperatures. When variables such as LWP had a huge influence upon brightness temperatures, little perceived benefit derived from detailed study of other variables, e.g., the cloud base height, that provided extremely minor influence over a reasonable range of values. The 'High' classification generally pertained to variables that caused a brightness temperature variation exceeding about 10° K. over a reasonable range of values. Similarly, the 'Medium' classification generally pertained to variables that influenced brightness temperatures in an amount ranging from 5° to 10° K. and the 'Low' classification pertained to variables with less than about 5° K. influence. Of course, these variable classifications change if the Base State assumptions are altered.

Example 2 teaches a preferred method for building confidence in the radiative transfer model that was developed according to step P102 of FIGS. 2, and 3, and implemented in Example 1. Confidence was built by comparing model results against well known statistical techniques that operate well under conditions where no ice is present in the atmosphere.

EXAMPLE 2

SENSITIVITY COMPARISONS AGAINST OTHER SYSTEMS

Calculation results from the forward-looking radiative transfer model that was developed according to FIGS. 2 and 3 were compared against the NOM algorithms according to Equations (1) and (2). Specifically, the radiative transfer model was used to calculate brightness temperatures for the 20, 30, and 90 GHz bands while sensitizing V and LWC. Brightness temperatures within the same general range were applied to Equations (1) and (2) to produce a set of comparative data partial derivatives of the brightness temperatures for each band were determined with respect to V and IWC. Two different sensitivity studies were performed in this manner. The first study utilized the base state data from Table 1, and assumed an atmospheric water profile as indicated in FIG. 5. A second system (State 2) was modified to eliminate the ice cloud shown in FIG. 5 at a height of from four km to six km. Table 2 below provides the comparison results.

TABLE 2

| | $\frac{\delta T_{B20.6}}{\delta p}$ | $\frac{\delta T_{B31.65}}{\delta p}$ | $\frac{\delta T_{B20.6}}{\delta LWP}$ | $\frac{\delta T_{B31.65}}{\delta LWP}$ |
|---|---|---|---|---|
| | $\delta v$ | $\delta v$ | $\delta LWP$ | $\delta LWP$ |
| NOAA Model | 11.72 | 4.76 | 245.07 | 561.50 |
| Base State | 9.0 | 4.3 | 310 | 625 |
| Difference % | 23 | 12.3 | −26.5 | −11.3 |
| State 2 | 10.04 | 4.23 | 273.06 | 514.40 |
| Difference % | 14.4 | 11.1 | 11.4 | −7.85 |

The Table 2 results build significant confidence in the radiative transfer system. Table 2 indicates that the FIG. 3 radiative transfer system for State 2 (i.e., in the absence of ice) provides a sensitivity to V and LWC that falls within fifteen percent of the calculation results for the NOAA algorithms. This level of agreement is very good when one considers that similar NOM algorithms have been shown to vary 8.7% for V and 37% for LWP from the radiosonde data that was used to create the NOAA algorithms. On the other hand, the Base State data varies up to 27% from the NOM algorithms. This variance exists because the Base State includes ice scattering. The NOM algorithms cannot account for ice scattering. Thus, it is seen that ice scattering produces a significant divergence from the NOM model, and the radiative transfer system is better able to account for the effects of ice scattering.

Step P106 of FIG. 2 requires a selection of sensitive variables that are subsequently used to generate a data set of brightness temperatures. Example 3 below provides a preferred method for implementing step P106.

EXAMPLE 3

GENERATION OF A BRIGHTNESS TEMPERATURE DATA SET

Based upon the results of Table 1 above, V, IWP, IWC, and $P_o$ were selected for further study. The remaining variables were assigned fixed values because they have a less significant influence upon brightness temperatures. Table 3 below lists the variables in combination with assumed values for the respective variables. Values assigned to the fixed variables represent year-round averages for the Denver, Col. area. Value ranges assigned to the sensitivity variables V, IWP, LWC, and $P_o$ indicate reasonable ranges for these variables based upon expert opinion.

TABLE 3

| Sensitivity Variables | Range | Unit |
|---|---|---|
| V | (0.4, 0.97) | cm |
| LWP | (0.0, 800.0) | g/m$^2$ |
| IWP | (0.0, 800.0) | g/m$^2$ |
| $P_o$ | (76.0, 86.0) | KPa |

| Fixed Variables | Fixed Value | Unit |
|---|---|---|
| $\rho$ | 0.5 | g/cm$^3$ |
| $r_e$ | 0.005 | cm |
| $H_b$ | 1.5 | km |
| $H_t$ | 2.0 | km |
| $T_A$ | −2.0 | °C. |
| $\Gamma$ | 6.0 | K/km |
| $H_{bi}$ | 3.5 | km |
| D | 1.0 | km |
| $D_i$ | 2.0 | km |

The values of Table 1 were used to generate a set of brightness temperature data through the radiative transfer system. A set of 1920 data groups including three brightness temperatures at each data group were generated by sampling the data ranges of interest for the variables V, IWP, LWP, and $P_o$ at uniform intervals, and randomly mixing the sample results to generate a combination of V, IWP, LWP, and $P_o$ for use as input into the radiative transfer system. The needed three-channel brightness temperatures are generated by the radiative transfer system.

Step P108 of FIG. 2 involves the use of a training data set to teach a neural network the solution for V, IWP, and LWP. The set of 1920 data points generated in Example 3 was intended for use as a neural network training data set.

NEURAL NETWORK SYSTEM APPLICATIONS

Neural network models are similar to statistical correlations because they provide correlations or algebraic expressions that are used to convert a system input into a system output. On the other hand, the neural network processing techniques that are used to develop the algebraic expression are quite different from statistical correlations. One example of a well known statistical correlation technique is the multiple order least squares fit that calculates a polynomial expression which defines a line having a minimum error determined with respect to a plurality of data points. These steps of statistical curve-fitting techniques are difficult or impossible to perform if many variables (e.g., thirteen variables) influence the calculation, or if there exist nonlinear relationships between the many variables. It can be extremely difficult to incorporate auxiliary measurement data into statistical correlations. Neural network techniques overcome these difficulties by mapping an input vector to an output vector through the application of weighing factors to the system inputs.

Neural network processing techniques are well known, and can be accomplished on a variety of software that is available to the public, such as the Neural Network add-on package available from SAS Institute, Inc., of Cary, N.C., or the Neurowindows package from Ward Systems Group, Inc., of Frederick, MD. There exist many different varieties of neural network processing. While a comprehensive presentation of all known neural network processing techniques is beyond the scope of this discussion, a brief overview of the neural network theory that is presently employed suffices to explain the preferred techniques to those skilled in the art.

Figure 6:
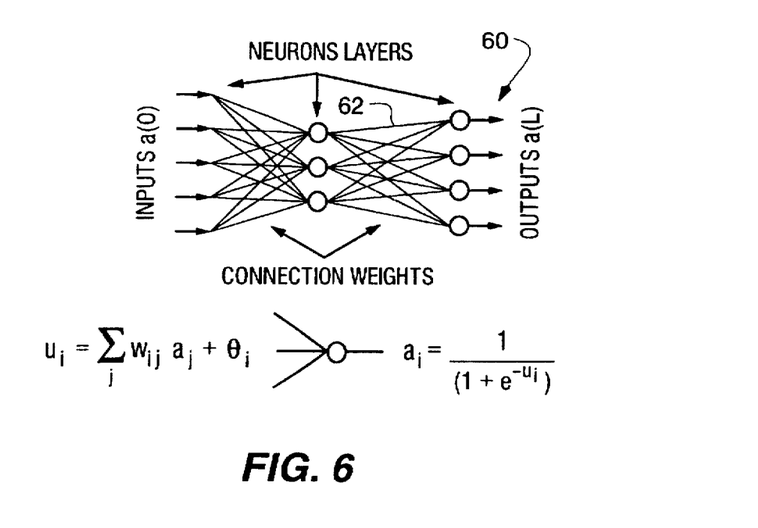
FIG. 6 depicts a neural network system in the form of a classical feed-forward multi layer perceptron.

FIG. 6 depicts the classical operation of a neural network processing algorithm 60 that is commonly referred to as a feed-forward multi layer perceptron. Algorithm 60 is a parameterized mapping process that relates an input vector a(O) to an output vector a(L) through the function $\phi$:

$$\bar{a}=(l)=\phi(\overline{W},\bar{a}(O)) \quad (21)$$

wherein W is the vector of weights; L is the number of layers in the network, and the remaining variables are defined above. According to Equation (20) in the context of FIG. 6, passing an input vector a(0) through algorithm 60 to arrive at an output vector a(L) includes taking the inner product of W times a(O) and feeding this product to a nonlinear system of neurons, e.g., neuron 62.

In feed-forward systems, algorithm 60 is trained to arrive at a correct answer by adjusting the weighing factors W to reduce or minimize the discrepancy between a target vector t and the output vector a(L). System inputs a(O) include brightness temperatures from a training data set (e.g. the data set of 1920 groups derived from Example 3), and also preferably include other relevant data that is known to influence the system inputs a(O) or the system outputs a(L). An example of other relevant data includes surface pressure $P_o$, which can be provided as both a system input $a(O)_i$ and a system output $a(L)_i$. The inclusion of this type of other relevant data often enhances the reliability of a neural network system. The training data set also includes a set of target input data points, e.g., the 1920 sets of V, IWP, LWP, and $P_o$ input parameters that were used to generate a corresponding set of 1920 brightness temperatures.

The object of neural network processing is to minimize the discrepancy between the target vector t and the output vector a(L). This discrepancy is commonly referred to as the cost function, and is most often defined as the sum squared error E of the output units of the vector a(L), i.e.:

$$E=\frac{1}{2}(t-\bar{a}(L))^T(t-\bar{a}(L))$$

wherein t is the target data vector; superscript T is a vector transposition function; E is the difference between the squares of the vector t and a(L); and the remaining variables are defined above.

Back propagation is used to compute a gradient of the cost function E to minimize the cost. Equation (22) sets forth the Back propagation algorithm:

$$\overline{W}^{(n+1)} \leftarrow \overline{W}^n - \eta \frac{E}{\partial \overline{W}^{(n)}} + \mu \Delta \overline{W}^{(n+1)} \quad (23)$$

wherein $\mu$ is a learning rate parameter, $\Delta$ is a momentum parameter; n is an iteration count; W are weight vectors; and the remaining variables are defined above. Thus, numerous iterations of algorithm 60 are performed with different weighing factors to arrive at a solution or output vector a(L) having an acceptably low error. It is a common practice to provide the initial output vector and weighing factors as an initial guess for what the values should be. The initial guess provides an inherent bias to the neural network system, but this bias is reduced or completely eliminated as successive iterations provide additional weighing factors that minimize the cost function.

Figure 7:
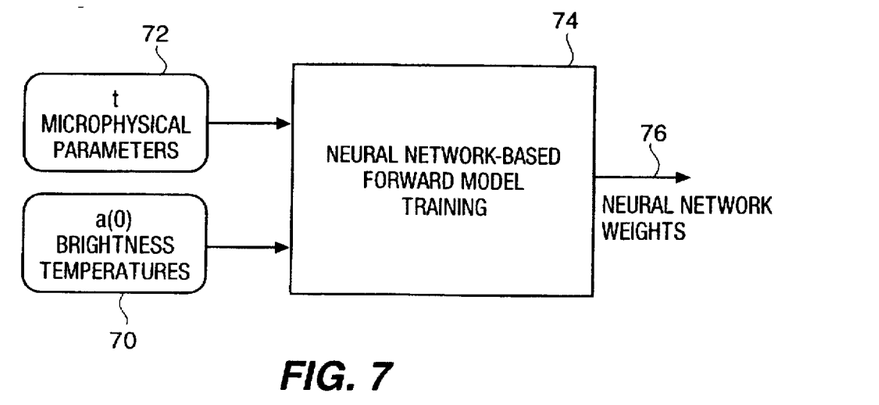
FIG. 7 depicts a schematic diagram showing the training phase of a forward neural network system.

FIG. 7 schematically depicts the operation of a neural network based on forward system training. A training data set including an input vector a(O) of brightness temperatures and a target data set t of microphysical parameters 72. The forward system operates according to Equation (20) to map the brightness temperatures 70 to an output vector a(L). The cost of this mapping is minimized according to Equations (21) and (22) to produce optimum weights 76.

EXAMPLE 4

A FORWARD AND INVERSE MODEL CONSTRUCTION USING MLP

Step P108 of FIG. 2 was conducted by applying the data set of 1920 data groups as input to a forward and inverse model construction iterative neural network algorithm. The system had four input units including V, IWP, LWP, and $P_o$. The system also had four output units including $T_{B20}$, $T_{B30}$, $T_{B90}$, and $P_o$. The system had one hidden layer with twenty-five neurons. After 5000 iterations, the output error was 0.000867 indicating that the neural network model on average produced very close agreement with the training data set.

The system was checked against an independent data set to determine whether the system would produce accurate results. The microphysical parameters in Table 3 were accessed to compute a time series of V, LWP, IWP, and $P_o$ profiles. The profiles were selected to represent an atmospheric condition including the presence of ice, an ice-free condition, and an atmospheric condition including both ice and liquid water clouds.

Figure 8:
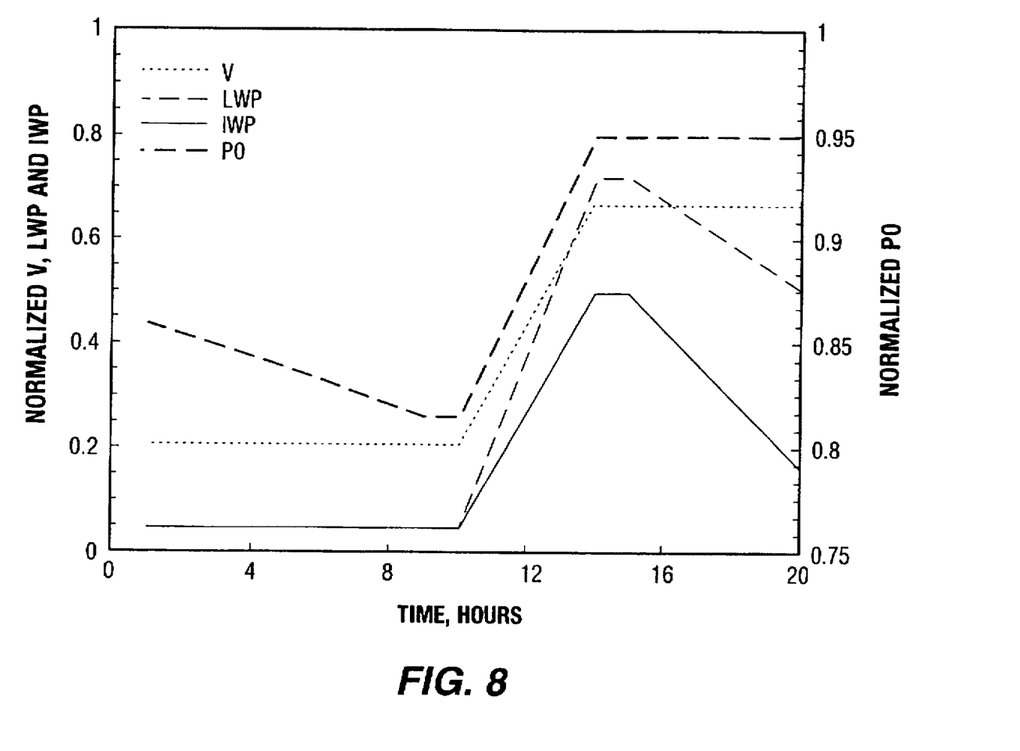
FIG. 8 depicts a time sensitive atmospheric water profile at locations above the FIG. 1 radiometer.
Figure 9:
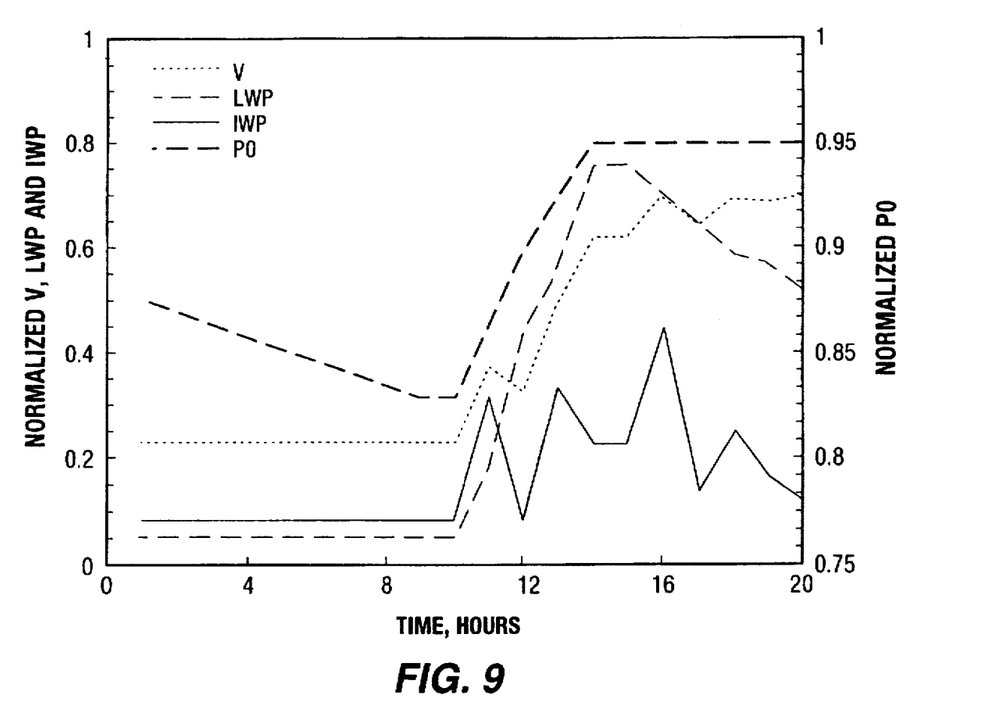
FIG. 9 depicts system outputs from the forward neural network that was trained according to FIG. 7 and which attempted to approximate the FIG. 8 atmospheric water profile.

FIG. 8 depicts the selected profiles, which are independent of the training data set generated in Example 3. The radiative transfer model of FIG. 2 (step P102) was used to generate three channel brightness temperatures at the 20, 30, and 90 GHz bands. These brightness temperatures were applied to the forward iterative neural network solution, which calculated values for V, IWP, LWP, and $P_o$. FIG. 9 depicts the time-dependent values for V, IWP, LWP, and $P_o$ that were retrieved from the neural network system. The neural-based values closely agree with the FIG. 8 values for these same parameters (i.e., within about ten percent). Nevertheless, the neural-based IWP values show a wild fluctuation between 10 and 20 hours, and are 0.03 mm greater than the corresponding FIG. 9 values between 0 and 10 hours. These results showed that the comparison with the independent data set had regions of significant variations despite the fact that the model on average produced good agreement with the training data set. While these variations did not preclude use of the forward and inverse neural network model in detection system 20 (see FIG. 1), it was believed that a better model could be selected.

Example 5 below shows that the FIG. 2 signal processing technique is improved by using another neural network solution in Step P108.

EXAMPLE 5

AN ITERATIVE INVERSE NEURAL NETWORK SOLUTION

As an alternative to the iterative neural network solution that was applied in Example 4, it is also possible to use an iterative neural network that holds the weighing factors constant while updating the inputs of forward systems to minimize the cost function. Conceptually, the idea of an iterative neural network system is to repeatedly present outputs to the forward system and search for a solution in the input space of the system while freezing the weights of the system. More specifically, the inversion algorithm is performed by computing the gradient of the cost function or Equation (21) with respect to the activation of the input units, and applying the iterative gradient descent algorithm according to Equation (23) to minimize the cost $$\bar{a}(0)^{(n+1)} \leftarrow \bar{a}(0)^{(n)} - \qquad (24)$$

$$(1-\mu)\left(\eta \frac{\partial \bar{E}}{\partial \bar{a}(0)^{(n)}} / \| \frac{\partial \bar{E}}{\partial \bar{a}(0)^{(n)}} \| - \mu \Delta \bar{a}(0)^{(n-1)}\right)$$

Figure 10:
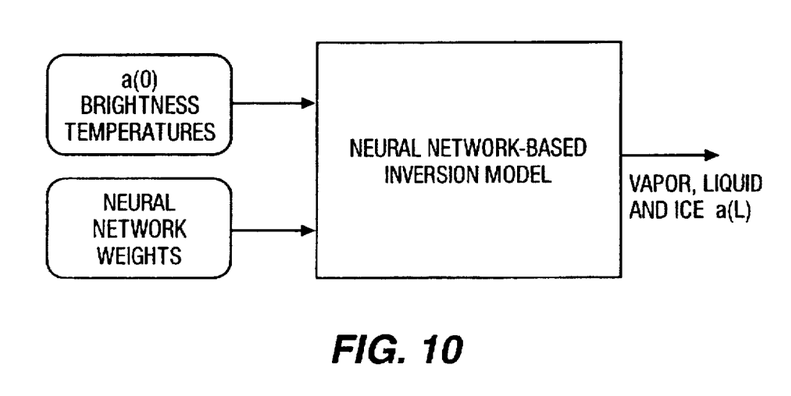
FIG. 10 depicts a schematic diagram showing the training phase of an iterative inversion neural network system.

FIG. 10 schematically depicts the operation of an iterative neural network system that was programmed into computer 26. The model training system included input vector a(O) of brightness temperatures 78, and a corresponding set of weighing factors 80. The weighing factors were the same as those developed for the forward neural network system 74 of FIG. 7. A conventional iterative inversion algorithm 82 applied Equation (19) to calculate an input vector 78 (brightness temperatures) from a data set including V, IWP, LWP, and $P_o$. Equations (21) and (23) were applied with the result of finding the closest approximation in the input data set.

The set of 1,920 data points from Example 3 was used as input data for an inverse neural network algorithm. As before, the radiative transfer system was applied to the microphysical parameters of FIG. 9 to generate a time-dependent set of brightness temperatures. These brightness temperatures were applied as system inputs to the iterative inverse system of FIG. 10. The results overcame many of the problems observed in Example 4.

Figure 11:
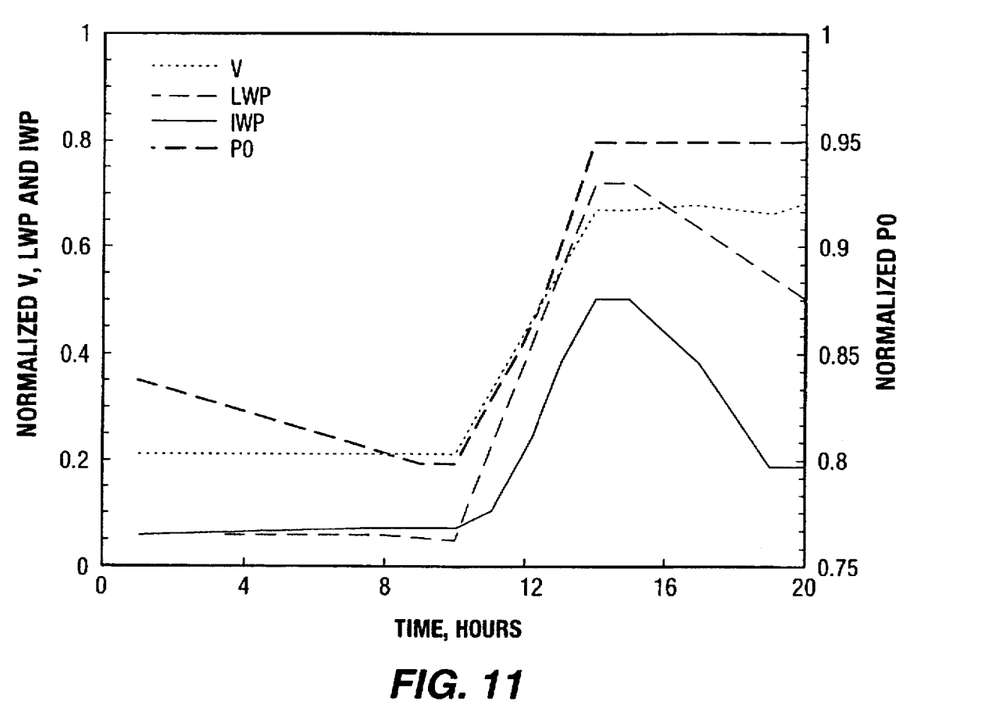
FIG. 11 depicts system outputs from the iterative inversion neural network that was trained according to FIG. 10 and which attempted to approximate the FIG. 8 atmospheric water profile.

FIG. 11 depicts the inverted neural network results. These results agree even more closely with the FIG. 8 data than did the forward neural network results of FIG. 9.

CALIBRATION OF THE NEURAL NETWORK SYSTEM

Step P110 of FIG. 2 includes a calibration of the neural network system. Until this step, no effort has been made to force the mathematical model into agreement with actual physical measurements. Example 6 below describes a preferred calibrating the neural network system according to step P110 of FIG. 2.

EXAMPLE 6

CALIBRATION OF THE FORWARD NEURAL NETWORK SYSTEM

The NOAA equations (1) and (2) do a good job of estimating V and LWP when there is no ice present in the atmosphere, but can not account for the presence of ice. The parameterized system according to the present invention accounts for the presence of ice by combining physical laws with statistical observations, but includes some inherent bias or error because no one mathematical model can fully explain the complex interaction between radiation and materials in the atmosphere. The accuracy of the parameterized system is, accordingly, enhanced by calibration against statistical correlations that perform well when there is no ice present in the atmosphere.

Actual radiometer data was collected in the field for this example. Three channel radiometer data for the 20, 30, and 90 GHz bands were collected on Mar. 22, 1994 from a radiometer in Erie, Col. Surface pressure was recorded simultaneously with the three-channel brightness temperatures. The measurement data set included 5000 measurements. The atmosphere was free of clouds with zero cloud liquid water. The vapor column varied between 0.4 and 0.6 mm.

The brightness temperatures at 20.6 and 31.65 GHz were applied to the NOM Equations (1) and (2) to generate L and LWP values. IWP was assumed to be zero as a consequence of visible atmospheric conditions indicating no clouds. Thus, a first group of 5000 data sets included NOM-based V and LWP values together with measured brightness temperatures corresponding to the 20, 30, and 90 GHz bands. These 5000 data points were used as a 'truth' data set to calibrate the neural network system, as described below.

The 5000 V and LWP values derived from Equations (1) and (2) were used as input to a forward neural network solution using the same weighing factors derived from Example 5. The system, accordingly, provided brightness temperatures. This calculation generated a second group of 5000 data sets including the NOM derived V and LWP values together with neural network derived brightness temperatures for the 20, 30, and 90 GHz bands.

The respective brightness temperatures at each wavelength for the two groups of data sets were subtracted from one another according to Equations (20)–(22) below:

$$T_{M20} - T_{C20} = \Delta T_{20} \quad (25)$$

$$T_{M30} - T_{C30} = \Delta T_{30} \quad (26)$$

$$T_{M90} - T_{C90} = \Delta T_{90} \quad (27)$$

wherein $T_{M20}$, $T_{M30}$, and $T_{M90}$ are the measured brightness temperatures for the corresponding 20, 30, and 90 GHz bands associated with a selected V and LWP; $T_{C20}$, $T_{C30}$, and $T_{C90}$ are the neural network-derived brightness temperature for the corresponding 20, 30, and 90 GHz bands associated with the selected V and LWP; and $\Delta T_{20}$, $\Delta T_{30}$, and $\Delta T_{90}$ are brightness temperature differences at the respective bands.

The differences $\Delta T_{20}$, $\Delta T_{30}$, and $\Delta T_{90}$, were plotted as histograms, and showed a bell-curve shape having an arithmetic mean. The means and standard deviation of the neural network system biases at each band were 1.503° K. and 0.223° K. at 20.6 GHz; 0.984° K. and 0.135° K. at 31.65 GHz; and 0.389° K. and 0.389° K. at 90 GHZ. These results showed that the neural network brightness temperature input data could be corrected to provide more accurate water content results by adjusting the input data to compensate for the observed mean difference values at each band.

The second group of 5000 data points was adjusted to compensate for the mean bias at each band by adding the mean for each band to each temperature at that band. The adjusted brightness temperatures were applied as input to an inverse neural network algorithm using the same weighing factors derived in Example 5, and used to generate V, LWP, and IWP values. The results for V and IWP were substantially identical to the NOM results. Thus, the calibration removed the inherent bias in parameterized system under conditions of no ice in the atmosphere.

Those skilled in the art understand that the preferred embodiments, as hereinabove described, may be subjected to apparent modifications without departing from the true scope and spirit of the invention. The inventor, accordingly, hereby states his intention to rely upon the Doctrine of Equivalents, in order to protect his full rights in the invention.

I claim:

1. A microwave radiometer system for use in measuring atmospheric water content, comprising:

means for passively detecting an intensity of atmospheric radiation in a plurality of frequency bands, and for providing signals representative of said intensity in each band;

means responsive to receipt of said signals for converting said signals to brightness temperature values corresponding to said plurality of bands;

means for simultaneously processing said brightness temperature values to produce data indicative of atmospheric water content including water vapor, cloud water, and ice.

2. The system as set forth in claim 1 wherein said detecting means includes means for selecting said plurality of bands at frequencies corresponding to features of the radiation absorption and emission spectrum of water in a particular phase.

3. The system as set forth in claim 2 wherein said frequencies are selected to correspond to the radiative transfer for different phases of water.

4. The system as set forth in claim 3 wherein said different phases of water include vapor, liquid, and ice phases of water.

5. The system as set forth in claim 4 wherein said plurality of bands include frequencies in the 20 GHz, 30 GHz, and 90 Hz bands.

6. The system as set forth in claim 1 wherein said plurality of bands include frequencies at 20.6 GHz, 31.65 GHz, and 90 GHz.

7. The system as set forth in claim 1 wherein said detecting means is operably configured to detect radiation from an atmospheric region consisting essentially of the atmosphere in direct vertical alignment above said detecting means.

8. The system as set forth in claim 1 wherein said processing means includes neural network means which receives said brightness temperatures as input and produces as output said data indicative of atmospheric water content including water vapor, cloud water, and ice.

9. The system as set forth in claim 8 wherein said neural network system includes an iterative inversion neural network system.

10. The system as set forth in claim 8 wherein said neural network means includes weighting factors derived from a parameterized system providing means for combining statistical information with information from physical laws to yield said atmospheric water content.

11. The system as set forth in claim 10 wherein said parameterized weighting factors derive from a means for calculating microwave scattering due to the scattering effects of atmospheric ice particles.

12. The system as set forth in claim 8 including means for calibrating said neural network system by adjusting said brightness temperatures for differences between physical measurements and system output from said neural network system.

13. The system as set forth in claim 12 wherein said calibrating means includes means for calculating a mean difference in brightness temperatures between the system output and physical observations, and adjusting said synthetic data set to reflect said mean difference.

14. A method of operating a radiometer to measure atmospheric water content, said method comprising the steps of:

detecting naturally occurring atmospheric microwave radiation in a plurality of bands;

providing signals representative of said microwave radiation in each band;

using said signals to determine respective brightness temperatures corresponding to said plurality of bands; and processing said brightness temperatures in a simultaneous manner to determine atmospheric water content including water vapor, cloud water, and ice.

15. The method as set forth in claim 14 wherein said detecting step includes a step of selecting said plurality of bands at frequencies corresponding to features of the radiative transfer for water.

16. The method as set forth in claim 15 wherein said selecting step includes selecting said frequencies to correspond to the radiative transfer for different phases of water.

17. The method as set forth in claim 16 wherein said different phases of water include vapor, liquid, and ice phases of water.

18. The method as set forth in claim 15 wherein said selecting step includes a step of selecting said frequencies in the 20 GHz, 30 GHz, and 90 Hz bands.

19. The method as set forth in claim 14 wherein said processing step includes a step of associating said brightness temperatures with said atmospheric water content through the use of a neural network.

20. The method as set forth in claim 19 wherein said neural network system includes an iterative inversion neural network system.

21. The system as set forth in claim 19 including a step of deriving weighting factors from a parameterized system that combines statistical information with information from physical laws to yield said atmospheric water content.

22. The system as set forth in claim 21 wherein said deriving step includes a step of calculating microwave scattering due to the scattering effects of atmospheric ice particles.

23. The system as set forth in claim 19 including a step of calibrating said neural network system by correcting said brightness temperatures for observed differences between a truth data set and system output from said neural network system.

24. The system as set forth in claim 23 wherein said calibrating step includes a step of calculating a mean difference in brightness temperatures between the system output and physical observations.

25. The method as set forth in claim 14 wherein said detecting step includes a strep of selecting at least one of said bands for sensitivity to radiation scattering effects.

* * * * *